(12) United States Patent
Kamei et al.

(10) Patent No.: US 9,145,568 B2
(45) Date of Patent: Sep. 29, 2015

(54) METHOD FOR PRODUCING ETHANOL USING BASIDIOMYCETE

(75) Inventors: Ichiro Kamei, Miyazaki (JP); Sadatoshi Meguro, Miyazaki (JP); Ryuichiro Kondo, Fukuoka (JP); Toshio Mori, Fukuoka (JP); Hirofumi Hirai, Shizuoka (JP)

(73) Assignees: University of Miyazaki, Miyazaki (JP); Kyushu University, National University Corporation, Fukuoka (JP); National University Corporation Shizuoka University, Shizuoka (JP)

( * ) Notice: Subject to any disclaimer, the term of this patent is extended or adjusted under 35 U.S.C. 154(b) by 0 days.

(21) Appl. No.: 14/122,893

(22) PCT Filed: Mar. 2, 2012

(86) PCT No.: PCT/JP2012/055444
§ 371 (c)(1),
(2), (4) Date: Nov. 27, 2013

(87) PCT Pub. No.: WO2012/164990
PCT Pub. Date: Dec. 6, 2012

(65) Prior Publication Data
US 2014/0154763 A1 Jun. 5, 2014

(30) Foreign Application Priority Data

May 31, 2011 (JP) .................. 2011-122579

(51) Int. Cl.
C12R 1/645 (2006.01)
C12P 7/10 (2006.01)
C12P 7/06 (2006.01)

(52) U.S. Cl.
CPC . *C12P 7/10* (2013.01); *C12P 7/065* (2013.01); *C12R 1/645* (2013.01); *Y02E 50/16* (2013.01); *Y02E 50/17* (2013.01)

(58) Field of Classification Search
None
See application file for complete search history.

(56) References Cited

U.S. PATENT DOCUMENTS

2012/0064574 A1 3/2012 Tokuyasu et al.

FOREIGN PATENT DOCUMENTS

| JP | 2001-169775 A | 6/2001 |
|---|---|---|
| JP | 2006-223159 A | 8/2006 |
| JP | 2007-319114 A | 12/2007 |
| JP | 2008-006372 A | 1/2008 |
| JP | 2008-054676 A | 3/2008 |
| JP | 2010-017084 A | 1/2010 |
| JP | 2010-183859 A | 8/2010 |
| JP | 2011-004730 A | 1/2011 |

OTHER PUBLICATIONS

Vares, T. et al. 1995. Lignin peroxidases, manganese peroxidases, and other ligninolytic enzymes produced by *Phlebia radiata* during solid-state fermentation of wheat straw. Applied and Environmental Microbiology (61)10: 3515-3520. specif. p. 3515.*

Gabriel, Maurice, "Plant Physiology: Alcohol fermentation by two types of basidiomycetes (*Phlebia radiate* Fr. and *Corticium ochraceofulvum* Bourd. & Galz.)," Compt. Rend., 1962, vol. 254, pp. 2213-2214.

Hirota et al., "Direct Fermentation of Ethanol From Cellulose Substrate using White-Rot Fungi," Moku-Kagaku Jyoho, 18(Suppl):25-26, Aug. 26-27, 2011, A Summary of Lectures in the 18th Annual Meeting of the Japan Wood Research Society.

Kenji Okamoto et al., "Alcohol Hakkosei Tanshikin no Tansaku to Seishitsu", Japan Society for Bioscience, Biotechnology, and Agrochemistry Taikai Koen Yoshishu, 2009, vol. 2009th, p. 100, #2P0799A.

Maurice, G., Fermentation Alcoolique par deux Basidiomycete *Phlebia dariata* Fr. et *Corticium ochracefulvum*, Compt. Rend., 1962, vol. 254, pp. 2213-2214, Gabriel Maurice.

Motoki Yoneda et al "Peniphora cinerea ni yoru Ethanol Seisan", Japan Society for Bioscience, Biotechnology, and Agrochemistry Taikai Koen Yoshishu, 2010, vol. 2010th, p. 72, 2APp15.

PCT/JP2012/055444 International Search Report mailed Mar. 27, 2012.

* cited by examiner

*Primary Examiner* — John S Brusca
*Assistant Examiner* — Sharon M Papciak
(74) *Attorney, Agent, or Firm* — Foley & Lardner LLP

(57) ABSTRACT

An object of the present invention is to provide a means for conveniently producing ethanol with high efficiency from a carbon source derived from a plant biomass resource or the like. The present invention relates to a method for producing ethanol, comprising a step of generating ethanol by culturing basidiomycetes belonging to the genus *Phlebia* with a carbon source. As carbon sources, cellulose, hemicellulose, glucose, xylose, and the like or plant biomass resources containing the same can be used.

5 Claims, 4 Drawing Sheets

METHOD FOR PRODUCING ETHANOL USING BASIDIOMYCETE

CROSS-REFERENCE TO RELATED APPLICATIONS

This application is a national phase of international application PCT/JP2012/055444, filed Mar. 2, 2012, which was published on Dec. 6, 2012, as WO 2012/164990, which claims the benefit of Japanese application No. 2011-122579, filed May 31, 2011. The respective contents of each of these applications are incorporated herein by reference in their entirety.

TECHNICAL FIELD

The present invention relates to a method for producing ethanol using basidiomycetes from a carbon source (preferably plant biomass such as polysaccharides in water-insoluble forms (e.g., cellulose, hemicellulose and starch) and saccharides (e.g., glucose and xylose)).

BACKGROUND ART

Technology for producing ethanol from a plant biomass material has been actively developed in recent years.

In general, ethanol production from a plant biomass material containing cellulose and/or hemicellulose in a water-insoluble form requires at least a saccharification step and an ethanol fermentation step, or may separately require a delignification step as a pretreatment for the saccharification step.

Examples of a general saccharification step include a sulfuric acid method and an enzyme method. The sulfuric acid method is problematic in high environmental load and corrosion of a reactor. The enzyme method is problematic due to the high cost of cellulase. A biomass resource should generally be pretreated through delignification before being subjected to the enzyme method. An alkaline treatment method and the like are known as delignification steps. The ethanol fermentation step is generally performed using yeast. As described above, a conventional method for producing ethanol from a biomass material requires multiple steps (with multiple stages).

For example, Patent Document 1 discloses a method for producing a substrate for an enzymatic saccharification reaction from a lignocellulose-based biomass raw material through a step involving alkaline treatment; that is, a method for pretreatment of a lignocellulose-based biomass raw material for a saccharification step. In this document, the thus produced substrate is saccharified by an enzyme, and the saccharified product is then further subjected to ethanol fermentation by a microorganism (yeast).

Patent Document 2 describes a saccharification and fermentation system using woody biomass as a raw material. In this system, a step of performing saccharification and fermentation reactions upon the woody biomass using a cellulose-degrading enzyme, a hemicellulose-degrading enzyme, and an alcohol-fermenting microorganism (yeast), and a step of performing a fermentation reaction using a microorganism (yeast) capable of separating a pentose substance remaining in the reaction product, and alcohol-fermenting pentose are implemented.

Patent Document 3 describes a method by which enzymatic saccharification and alcoholic fermentation are performed in the same fermenter. However, even this method requires the combined use of a microorganism such as filamentous fungi capable of producing a saccharifying enzyme and yeast capable of performing alcoholic fermentation.

As described above, conventional technology for producing ethanol from a plant biomass material requires multiple steps (with multiple stages), and thus is not satisfactory in terms of energy consumption and cost. Technology for implementing a delignification step, a saccharification step, and an ethanol fermentation step with the use of a single means has been required.

Plant biomass materials such as rice straws, bamboos, and hardwood lumber contain hemicellulose, which contains a pentose (e.g., xylose) as a constituent unit. However, general ethanol-fermenting microorganisms are not capable of assimilating a pentose to generate ethanol. Therefore, the production of ethanol using a general ethanol-fermenting microorganism from a saccharified product of hemicellulose is problematic, in that the pentose cannot be used and the ethanol yield is lowered. As described in Patent Document 2, the combined use of a microorganism capable of assimilating a hexose such as glucose, so as to ferment and generate ethanol and a microorganism capable of assimilating a pentose such as xylose, so as to ferment and generate ethanol is problematic in terms of cost and the resulting complicated reaction system.

Patent Document 4 discloses a method for producing alcohol from a carbon source by alcoholic fermentation using *Trametes suaveolens* as technology that enables implementation of a delignification step, a saccharification step, and an ethanol fermentation step with a single means. However, in Patent Document 4, *Trametes suaveolens* was confirmed to be able to assimilate hexose, however, whether or not *Trametes suaveolens* is capable of simultaneously assimilating pentose and hexose was not confirmed. Specifically, technology, by which a delignification step, a saccharification step, and an ethanol fermentation step can be implemented using a single means, which would allow both hexose and pentose to be ethanol fermented as carbon sources, has not yet been established.

*Trametes suaveolens* used in Patent Document 4 is a type of white-rot fungi. White-rot fungi are known to have the ability to produce lignin peroxidase, manganese peroxidase, laccase, and the like and to degrade wood-derived lignin (Patent Document 5). White-rot fungi are also known to have the ability to saccharify cellulose. The *Phlebia* sp. MG-60 strain belonging to the genus *Phlebia* has been isolated as a type of white-rot fungi, which is capable of degrading lignin under hypertonic conditions (Patent Document 6). Whether or not white-rot fungi belonging to the genus *Phlebia* has the ability to ferment alcohol has conventionally remained unexamined.

CITATION LIST

Patent Documents

Patent Document 1: JP Patent Publication (Kokai) No. 2011-4730A
Patent Document 2: JP Patent Publication (Kokai) No. 2010-17084A
Patent Document 3: JP Patent Publication (Kokai) No. 2008-54676A
Patent Document 4: JP Patent Publication (Kokai) No. 2010-183859A
Patent Document 5: JP Patent Publication (Kokai) No. 2008-6372A
Patent Document 6: JP Patent Publication (Kokai) No. 2001-169775A

DISCLOSURE OF THE INVENTION

Problem to be Solved by the Invention

An object of the present invention is to provide a means for conveniently producing ethanol with high efficiency from a carbon source derived from a plant biomass resource or the like.

Means for Solving the Problem

The present inventors have surprisingly discovered that basidiomycetes belonging to the genus *Phlebia* have not only the ability to degrade lignin and the ability to saccharify polysaccharides, but also the ability to generate ethanol from sugars, as well as the ability to generate ethanol using not only glucose but also xylose as a carbon source. The present inventors have further discovered that ethanol generation efficiency can further be increased by performing a pretreatment step involving the culturing of basidiomycetes belonging to the genus *Phlebia* with a lignin-containing carbon source under aerobic conditions, further culturing the basidiomycetes with the carbon source under semi-aerobic conditions or anaerobic conditions, and thus performing ethanol fermentation using the carbon source as a substrate. The present inventors have completed the following invention based on these findings. Specifically, the present invention encompasses the following (1) to (8):
(1) A method for producing ethanol, comprising a step of generating ethanol by culturing a basidiomycete belonging to the genus *Phlebia* with a carbon source.
(2) The method according to (1), wherein the step of generating ethanol comprises,
    a pretreatment step for culturing the basidiomycete with a carbon source under aerobic conditions, and
    a fermentation step for further culturing the basidiomycete with the carbon source under semi-aerobic conditions or anaerobic conditions after the pretreatment step, so as to generate ethanol.
(3) The method according to (1) or (2), wherein the basidiomycete belonging to the genus *Phlebia* is *Phlebia* sp. MKFC40001 (NITE BP-1099).
(4) The method according to any one of (1) to (3), wherein the carbon source is a polysaccharide.
(5) The method according to (4), wherein the polysaccharide is in the form of a plant biomass material, crystalline cellulose, paper, pulp, or cotton linter.
(6) The method according to any one of (1) to (3), wherein the carbon source is at least one type of saccharides selected from the group consisting of glucose, xylose, mannose, galactose, fructose, and arabinose.
(7) An inoculum for generating ethanol from a carbon source, comprising a basidiomycete belonging to the genus *Phlebia*, and a carrier supporting the basidiomycete.
(8) The inoculum according to (7), wherein the basidiomycete belonging to the genus *Phlebia* is *Phlebia* sp. MKFC40001 (NITE BP-1099).

This description includes part or all of the contents as disclosed in the description and/or drawings of Japanese Patent Application No. 2011-122579, which is a priority document of the present application.

Effects of the Invention

According to the present invention, a means for conveniently producing ethanol with high efficiency from a carbon source derived from a plant biomass resource or the like is provided.

BEST MODE FOR CARRYING OUT THE INVENTION

1. Basidiomycete

Figure 1:
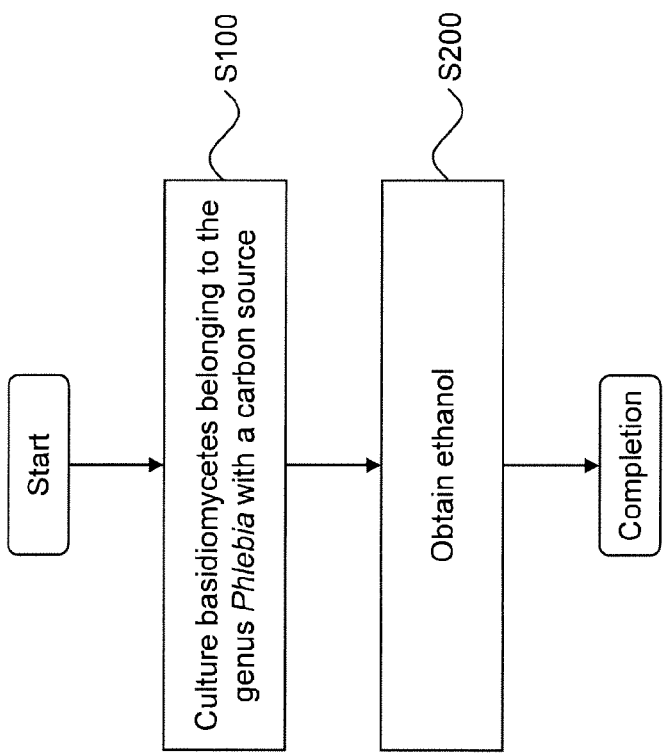
FIG. 1 shows a flow chart showing the summary of the method of the present invention.

The present invention is based on the remarkable finding that basidiomycetes belonging to the genus *Phlebia* have the ability to assimilate carbon sources in order to generate ethanol.

Basidiomycetes to be used in the present invention belonging to the genus *Phlebia* are not particularly limited, as long as they have the ability to generate ethanol when cultured with a carbon source described later. Basidiomycetes to be used in the present invention are more preferably white-rot fungi having the ability to degrade lignin, which is a wood cell wall component. An example of such a microorganism is *Phlebia* sp. MKFC40001 (NITE BP-1099, hereinafter, referred to as simply "MKFC40001"). MKFC40001 is a strain identical to *Phlebia* sp. MG-60 that is highly salt-tolerant white-rot fungi separated from tropical trees, as disclosed in Patent Document 6 and Applied and Environmental Microbiology 74 (9), pp. 2709-2716. The present inventors have obtained the *Phlebia* sp. MG-60 strain from the collection stored at Kyushu University. This strain was deposited in Japan under the name of *Phlebia* sp. MKFC40001 with the Incorporated Administrative Agency, Patent Microorganisms Depositary, National Institute of Technology and Evaluation (NITE) (2-5-8 Kazusakamatari, Kisarazu-shi, Chiba 292-0818, Japan) on May 11, 2011, and given the accession number of NITE P-1099. The *Phlebia* sp. MKFC40001 (NITE P-1099) deposited with the Incorporated Administrative Agency, Patent Microorganisms Depositary, National Institute of Technology and Evaluation (NITE) (2-5-8 Kazusakamatari, Kisarazu-shi, Chiba 292-0818, Japan) was transferred to and deposited internationally (international deposition) under the terms of the Budapest Treaty as of Feb. 21, 2012. *Phlebia* sp. MKFC40001 internationally deposited as of Feb. 21, 2012 was given the accession number of NITE BP-1099 by the aforementioned institute.

The taxonomic position and scientific properties of *Phlebia* sp. MKFC40001 (NITE BP-1099) are as described below.

Taxonomic position: As a result of analyzing the ITS-5.8S rDNA sequence (DDBJ accession number AB210077), *Phlebia* sp. MKFC40001 (NITE BP-1099) has been classified as a cluster of the genus *Phlebia* in the phylogenetic tree, and is 90% identical to and thus determined to be related to the *Phlebia* radiate strain ATCC64658.

Scientific properties: *Phlebia* sp. MKFC40001 (NITE BP-1099) is a type of white-rot fungi, which is a wood-rot fungus capable of degrading lignin, which is a component of wood cell walls. *Phlebia* sp. MKFC40001 grows well on PDA medium at 30° C. to form filamentous white hyphae. After spreading throughout the medium, it appears to be light yellow in color. When it is grown in 0.02% guaiacol-containing PDA medium, the medium appears to be red due to the presence of guaiacol oxide. Under low nitrogen conditions,

*Phlebia* sp. MKFC40001 produces a large amount of manganese peroxidase to oxidize a phenolic compound. *Phlebia* sp. MKFC40001 is a salt-tolerant microorganism that can grow well even in medium containing about 3% sea salts.

Examples of *Phlebia* sp. MKFC40001 to be used in the present invention include mutant strains of *Phlebia* sp. MKFC40001 substantially retaining the ability to generate ethanol when cultured with a carbon source described later. Here, the term "mutant strains" refers to mutant strains obtained via mutagenesis treatment of *Phlebia* sp. MKFC40001. Mutagenesis treatment can be performed using any appropriate mutagen. Here, the term "mutagen" refers not only to an agent having the effects of a mutagen, but also a treatment having the effects of a mutagen such as UV irradiation.

2. Carbon Source

Basidiomycetes belonging to the genus *Phlebia* has the ability to degrade lignin and the ability to saccharify polysaccharides, in addition to the ability to assimilate saccharides to generate ethanol. Thus various carbon sources can be used in the method of the present invention. Examples of a carbon source include saccharides, polysaccharides, polysaccharides in water-insoluble forms and polysaccharide-containing plant biomass resources.

Examples of saccharides that can be used as carbon sources include monosaccharides such as hexoses (e.g., glucose, mannose, galactose, and fructose), and pentoses (e.g., xylose and arabinose), and disaccharides such as cellobiose. A plant biomass material such as rice straws, bamboos, and hardwood lumber comprises hemicellulose containing a pentose such as xylose and a hexose such as glucose as constituent units, and cellulose containing glucose as a constituent unit. The method of the present invention exhibits an astounding effect that ethanol can be efficiently generated by a single step from a plant biomass material comprising hemicellulose and cellulose.

Furthermore, as a carbon source, polysaccharides (including oligosaccharides) that can be saccharified to supply the above saccharides can be used. Examples of polysaccharides include cellulose, hemicellulose, and starch. Polysaccharides may be in a water-insoluble form. Examples of water-insoluble polysaccharides that can be used as carbon sources (particularly, cellulose and/or hemicellulose) include polysaccharides in the form of a plant biomass material, crystalline cellulose, paper such as waste paper, pulp, cotton linter or the like.

A plant biomass material may be a woody plant biomass material or a herbaceous biomass material. Examples of a woody plant biomass material include wood (including scrap wood from construction, thinnings, and the like), sawdust, waste mushroom bed, and the like derived from trees such as conifer, hardwood, or gymnosperms. Examples of a herbaceous biomass material include materials derived from rice, wheat or barley or oat, corn, sugarcane, bamboos, Japanese pampas grass, and the like, such as residues resulting from harvesting and processing of agricultural products. A plant biomass material that is subjected in advance to physical treatment (e.g., grinding treatment and blasting treatment) or chemical treatment (e.g., alkaline treatment) can also be used as a carbon source.

3. Generation of Ethanol

The method for producing ethanol of the present invention comprises step S100 (FIG. 1) of generating ethanol by culturing basidiomycetes belonging to the genus *Phlebia* with a carbon source.

Culture conditions are not particularly limited. Typically, basidiomycetes belonging to the genus *Phlebia* are inoculated and cultured in a medium with an appropriate nature (e.g., liquid, solid, or slurry) containing the above carbon source together with necessary ingredients including a nitrogen source and an inorganic salt, as necessary. Basidiomycetes may be cultured by anaerobic culture, semi-aerobic culture, or aerobic culture, and preferably cultured by anaerobic culture or semi-aerobic culture. The term "anaerobic culture" or "semi-aerobic culture" specifically means to culture basidiomycetes inoculated in a medium without substantially exposing them to outside air. In the present invention, the term "anaerobic conditions" refers to culture conditions where substantially no free oxygen is present. For example, under such culture conditions, basidiomycetes and a medium are placed within a reactor, the atmosphere within the reactor is substituted with a nitrogen gas or the like to create a condition where no oxygen is substantially contained, and then basidiomycetes are cultured substantially without ventilation between the atmosphere within the reactor and outside air. The term "semi-aerobic conditions" in the present invention refers to culture conditions where the free oxygen level is reduced compared to that under air atmosphere. For example, under such culture conditions, basidiomycetes and a medium are placed within a reactor and the atmosphere within the reactor that is filled with air or the like (containing oxygen) at least at the initiation of culture and then basidiomycetes are cultured substantially without ventilation between the atmosphere within the reactor and outside air. The term "aerobic conditions" in the present invention refers to culture conditions where free oxygen is present to the same extent as that under air atmosphere. For example, under such culture conditions, basidiomycetes and a medium are placed within a reactor, and then they are cultured under a condition where ventilation is possible between the atmosphere within the reactor and outside air.

Other culture conditions can be appropriately determined. For example, the temperature preferably ranges from 25° C. to 35° C., and the time for culture ranges from about 24 hours to 500 hours.

In a preferred embodiment of the present invention, step S100 for generating ethanol by culturing basidiomycetes belonging to the genus *Phlebia* with a carbon source comprises at least 2 steps (FIG. 2): pretreatment step S 101 for culturing basidiomycetes belonging to the genus *Phlebia* with a carbon source under aerobic conditions; and, after pretreatment step S101, fermentation step S102 for generating ethanol by further culturing the basidiomycetes with the carbon source under semi-aerobic conditions or anaerobic conditions. This embodiment is particularly effective for a carbon source containing lignin such as a plant biomass material.

Pretreatment step S101 is a step for inoculating the basidiomycetes into a medium containing a carbon source and water as appropriate, and then culturing them under aerobic conditions. In the pretreatment step, lignin is degraded when the carbon source contains the lignin. The pretreatment step is preferably performed until the lignin content (in the total amount of the carbon source (on the dried basis)) becomes 20% (w/w) or less and preferably 15% (w/w) or less. The temperature for the pretreatment step preferably ranges from 25° C. to 35° C. The culture period for the pretreatment step ranges from preferably 250 to 3000 hours, more preferably 300 to 2000 hours, more preferably 500 to 1500 hours, and most preferably 500 to 1000 hours. The pretreatment step may be performed with a medium containing a carbon source and water as appropriate, which is further supplemented with necessary ingredients such as a nitrogen source and inorganic salts as necessary. When the carbon source is a plant biomass material or the like containing a nitrogen source, inorganic salts, and the like, the addition of additional ingredients is not essential.

Fermentation step S102 is a step for generating ethanol, comprising, after pretreatment step S101, further culturing the basidiomycetes with the carbon source under semi-aerobic conditions or anaerobic conditions. If necessary, necessary ingredients such as a nitrogen source and inorganic salts are added to a mixture containing the basidiomycetes and the carbon source after the pretreatment step, and then the fermentation step can be performed under semi-aerobic conditions or anaerobic conditions. The fermentation step is preferably performed at the temperature ranging from 25° C. to 35° C. for 120 to 720 hours and particularly preferably for 240 to 480 hours.

Figure 2:
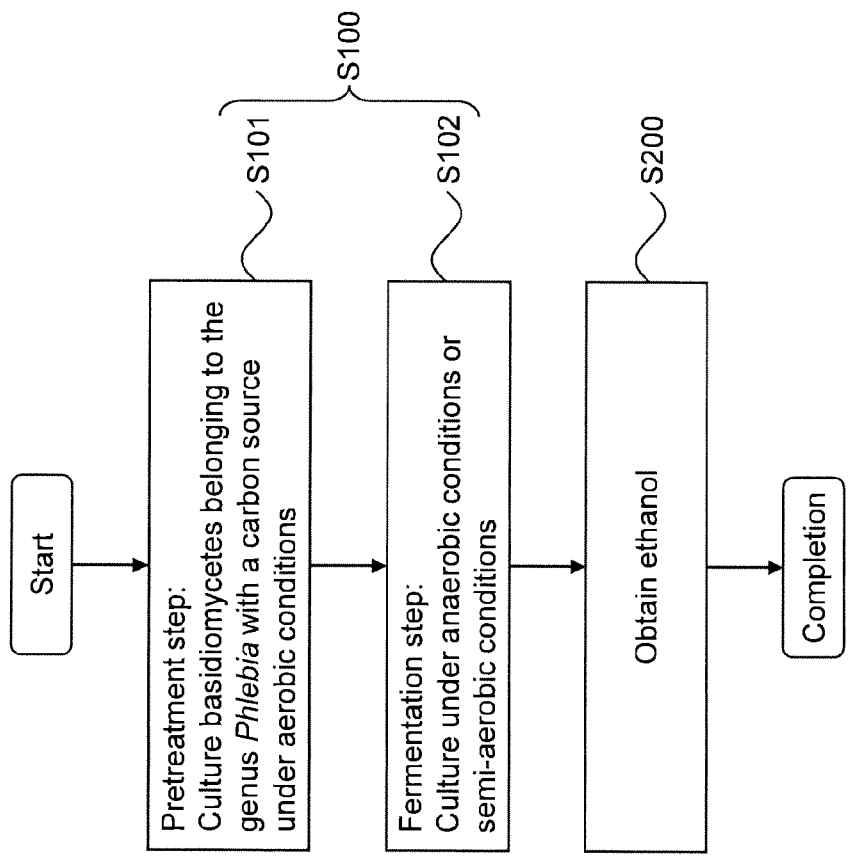
FIG. 2 is a flow chart showing the summary of a preferred embodiment of the method of the present invention.

Pretreatment step S101 and fermentation step S102 are preferably performed within the same reactor in order to efficiently perform the embodiment shown in FIG. 2.

In another embodiment, pretreatment step S101 is not essential. In this case, step S100 may be a step of culturing the basidiomycetes in the presence of a carbon source under preferably semi-aerobic conditions or anaerobic conditions and then generating ethanol without performing pretreatment step S101. This embodiment is appropriate for a case where a lignin-free carbon source (or a carbon source in which the lignin content is at the target level or less in the above pretreatment step) is used, for example. Step S100 in this case is preferably performed at the temperature ranging from 25° C. to 35° C. for preferably 24 to 720 hours, and particularly preferably for 48 to 480 hours.

Specific means in step S200 (FIG. 1 and FIG. 2) for collecting ethanol generated by culture from a medium are not particularly limited.

4. Inoculum

The present invention further provides an inoculum for generation of ethanol from a carbon source, containing a basidiomycete belonging to the genus *Phlebia* and a carrier supporting the basidiomycete.

The inoculum is a composition containing the mycelia of basidiomycetes with carriers in an appropriate form such as solid carriers or liquid carriers.

The present invention further relates to the use of an inoculum composition containing a basidiomycete belonging to the genus *Phlebia* and a carrier supporting the basidiomycete for generation of ethanol from a carbon source.

EXAMPLES

Experiment 1

1. Strains Used

*Phlebia* sp. MKFC40001 (NITE BP-1099 internationally deposited on Feb. 21, 2012, that is identical to NITE P-1099 deposited in Japan on May 11, 2011) was cultured at 28° C. for 7 days in a PDA (potato, dextrose, agar) plain medium and then the mycelia thereof were used for the following test.

The mycelia of similarly cultured wood-rot fungi (including the following 29 types of white-rot fungi) were also used for the following test.

*Ceriporia lacerate* (1 strain), *Phanerochaete sordida* (2 strains), *Phanerochaete chrysosporium* (1 strain), *Pleurotus ostreatus* (1 strain), *Pleurotus pulmonarius* (1 strain), *Pycnoporus coccineus* (3 strains), *Trametes versicolor* (2 strains), *Trametes hirsute* (2 strains), *Trametes suaveolens* (2 strains), *Gloeophyllum trabeum* (2 strains), *Fomitopsis palustris* (1 strain), *Punctularia* sp. (2 strains), and other unidentified strains (9 strains)

2. Culture Medium Composition and Culture Conditions

The culture composition was as follows:

TABLE 1

| | |
|---|---|
| Yeast extracts | 10 g/l |
| $KH_2PO_4$ | 10 g/l |
| $(NH_4)_2SO_4$ | 2 g/l |
| $MgSO_4 \cdot 7H_2O$ | 0.5 g/l |
| Carbon source | 20 g/l (or 10 g/l) |
| pH | 6.0 |

As carbon sources, glucose (Wako Pure Chemical Industries, Ltd., special class), xylose (Wako Pure Chemical Industries, Ltd., special class), crystalline cellulose (Cellulose microcrystalline: MERCK), unbleached hardwood Kraft pulp (Oji Paper Group), unbleached conifer Kraft pulp (Oji Paper Group), newspaper (lightly cut with a mixer), and *Quercus serrata* wood flour (100 mesh path, delipidated with methanol) were used.

Use of Glucose or Xylose as a Carbon Source:

A 100-ml Erlenmeyer flask containing 18 ml of a medium from which a carbon source had been removed was sterilized using an autoclave. A 20% aqueous glucose solution and a 20% aqueous xylose solution were filter-sterilized. The aqueous glucose solution (2 ml), or the aqueous xylose solution (2 ml), or both aqueous solutions (1 ml each) were added to the Erlenmeyer flask after autoclave sterilization to produce a final concentration of the carbon source of 2% in each medium. Each target strain cultured in the PDA medium was removed, together with the agar, using a cork borer (diameter: 5 mm), and inoculated in the Erlenmeyer flask. The flask was sealed with a silicon plug to block aeration. Static culture was then performed in an incubator set at 28° C.; that is, in the dark. Sample collection was performed on days 5, 10, and 20 of culture.

Use of crystalline cellulose, unbleached hardwood Kraft pulp, unbleached conifer Kraft pulp, newspaper, or *Quercus serrata* wood flour as a carbon source:

A predetermined carbon source was added to a 100-ml Erlenmeyer flask containing 20 ml of a medium from which a carbon source had been removed so that the concentration was 2% (w/v) or 1% (w/v) as shown in the following Table, followed by autoclave sterilization. Target strains were inoculated therein following the same procedures and conditions as those described above, the strains were cultured, and then sample collection was performed.

3. Analytical Method 1.5 ml of a liquid layer was collected from each medium after a predetermined period of culture. After centrifugation at 13,600 g×10 min and 4° C., 1.0 ml of a supernatant was collected. The thus collected supernatant was diluted 5-fold with sterile water, and then filtered through a filter (0.45 μm), thereby preparing each analytical sample. Analytical samples were analyzed by HPLC.

HPLC Conditions are as Follows.

Column: Shodex KS-802
Mobile phase: Distilled water
Flow rate: 1.0 ml/min
Detector Shimadzu RID-10A 4. Results From 30 types of wood-rot fungi subjected to the test, highly efficient ethanol fermentation with a theoretical yield of 70% or more with the use of glucose as a substrate was observed for 3 types (MKFC40001, *Punctularia* sp., and *Trametes suaveolens*). Highly efficient ethanol fermentation with a theoretical yield of 60% or more with the use of xylose as a substrate was observed for 1 type (MKFC40001). Highly efficient ethanol fermentation with a theoretical yield of 70% or more with the use of a glucose-xylose mixed system as a substrate was observed for 1 type (MKFC40001). Ethanol fermentation with the use of crystalline cellulose as a substrate was observed for only MKFC40001. MKFC40001 alone was able to generate ethanol from all types of substrate.

The results for MKFC40001 are shown in the following Table.

MKFC40001 produced ethanol with a theoretical yield of 70% or more from glucose on day 5 of culture. It was thus demonstrated that MKFC40001 has the high ability to ferment glucose.

MKFC40001 produced ethanol with a theoretical yield of 60% or more from xylose on day 10 of culture. It was thus demonstrated that MKFC40001 has the ability to ferment xylose.

MKFC40001 produced ethanol with a theoretical yield of 70% or more from a mixed solution of glucose and xylose on day 10 of culture. It was thus demonstrated that MKFC40001 is capable of simultaneously fermenting glucose and xylose.

It was confirmed that MKFC40001 is capable of performing ethanol fermentation directly from insoluble cellulose (crystalline cellulose).

It was confirmed that MKFC40001 performs ethanol fermentation directly from unbleached Kraft pulp (hardwood Kraft pulp and conifer Kraft pulp) obtained by Kraft digesting of wood.

It was confirmed that MKFC40001 performs ethanol fermentation directly from newspaper rich in lignin and impurities such as an ink.

It was confirmed that MKFC40001 performs ethanol fermentation directly from hardwood wood flour (*Quercus serrata*).

TABLE 2

Ethanol fermentation using *Phlebia* sp. MKFC40001 from glucose, xylose, glucose + xylose, crystalline cellulose, unbleached hardwood Kraft pulp, unbleached conifer Kraft pulp, newspaper, or *Quercus serrata* wood flour

| Fermentation substrate (w/v %) | Ethanol conversion*(%) | | |
|---|---|---|---|
| | Day 5 | Day 10 | Day 20 |
| Glucose (2%) | 73.3 | 72.5 | — |
| Xylose (2%) | 56.8 | 63.7 | — |
| Glucose (1%) + Xylose (1%) | 67.9 | 73.3 | — |
| Crystalline cellulose (1%) | 0 | 0 | 58.0 |
| Crystalline cellulose (2%) | 0 | 0 | 39.8 |
| Unbleached hardwood Kraft pulp (2%) | — | 64.3 | 70.3 |
| Unbleached conifer Kraft pulp (2%) | — | 19.4 | 42.4 |
| Newspaper (2%) | 39.9 | 50.5 | 51.1 |
| *Quercus serrata* wood flour (1%) | 0 | 0 | 41.1 |

*The theoretical yield was determined to be 100% when 2 moles of ethanol was produced from 1 mole of glucose.
*The theoretical yield was determined to be 100% when 5 moles of ethanol was produced from 3 moles of xylose.
*The amounts of microcrystalline cellulose, unbleached Kraft pulp, and newspaper were expressed in terms of the amount of glucose present after complete hydrolysis therefrom. The theoretical yield was determined to be 100% when 2 moles of ethanol was produced from 1 mole of glucose.
*Polysaccharide components contained in *Quercus serrata* wood flour were estimated to account for 50% and the amount thereof was expressed in terms of the amount of glucose present after complete hydrolysis therefrom. The theoretical yield was determined to be 100% when 2 moles of ethanol was produced from 1 mole of glucose.
*"—" indicates that no measurement was performed.

Experiment 2

1. Experimental Method

*Quercus serrata* wood flour (42-100 mesh) delipidated in advance with methanol was used as a fermentation substrate. Wood flour (total dry weight of about 0.8 g) was sampled in a 100-mL Erlenmeyer flask, and then pure water was added so that the percentage of water content was about 80%. After autoclave sterilization, *Phlebia* sp. MKFC40001 cultured in a PDA (potato, dextrose, agar) medium was bored together with the PDA medium using a cork borer, and then a section thereof was inoculated. The reactor was covered with an air permeable sponge plug made of a silicon resin (aerobic conditions) followed by culturing at 28° C. in the dark, so that delignification (pretreatment) of wood flour was performed. 20 mL of autoclave-sterilized fermentation medium (Table 1) was added to the Erlenmeyer flask after a predetermined period of culture (pretreatment) under aerobic conditions. The flask was then sealed with a silicon rubber plug (semi-aerobic conditions) followed by culturing at 28° C. in the dark. After culture, the culture solution was subjected to HPLC analysis, the amount of ethanol generated was measured, and then the percentage of ethanol conversion was estimated.

2. Analytical Method

The chemical composition of wood flour was analyzed according to a method disclosed by the National Renewable Energy Laboratory, U.S.A. (NREL). Specifically, each wood flour sample was subjected to sulfuric acid hydrolysis, and the thus obtained reducing sugars were analyzed by high performance liquid chromatography (HPLC). The glucose, xylose, galactose, and mannose detected were calculated as glucan, xylan, galactan, and mannan, respectively (Table 3). Regarding lignin, the total dry weight of the residues (acid-insoluble substances) resulting from the sulfuric acid hydrolysis of each wood flour sample was measured to determine the amount of lignin. The amount of the other components present was estimated by subtracting the thus calculated weights of glucan, xylan, galactan, mannan, and lignin from the total dry weight of the wood flour delipidated with methanol.

The amount of the thus generated ethanol was measured as follows. 1.5 ml of a liquid layer was collected from a medium after a predetermined period of culture. After centrifugation at 13,600 g×10 min and 4° C., the collected supernatant was diluted 5-fold with sterile water and then filtered through a filter (0.45 μm). The thus obtained sample was analyzed by HPLC. Ethanol conversion % is the percentage accounted for by the amount of actually generated ethanol, when the theoretical ethanol yield (when ethanol (2 moles) was produced from each of glucose, galactose, and mannose (1 mole) and when ethanol (5 moles) was produced from xylose (3 moles)) calculated from the sugar composition (Table 1) (to be used as a substrate for ethanol fermentation under semi-aerobic conditions) of each wood flour sample after pretreatment under aerobic conditions was designated as 100%.

3. Results and Discussion

Figure 3:
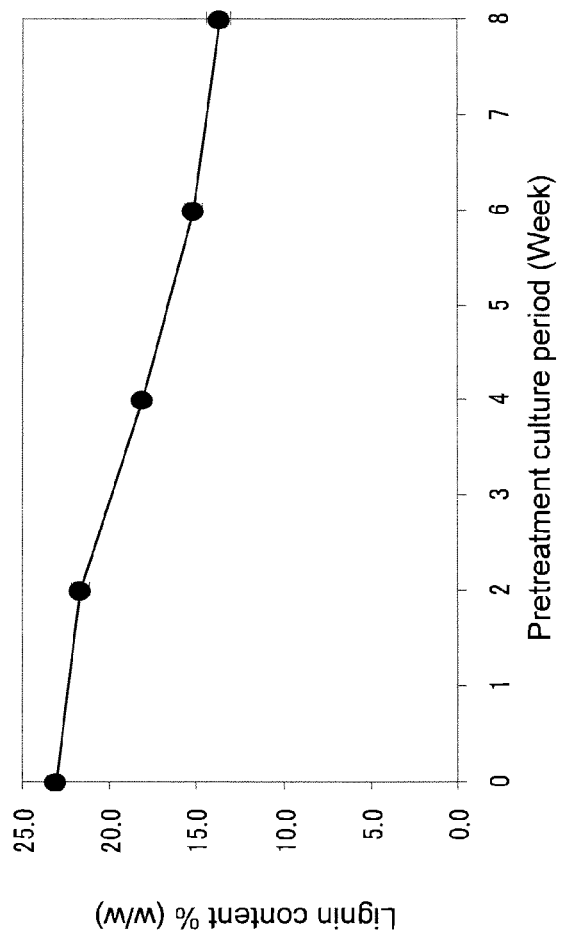
FIG. 3 is a graph showing the relationship between the period of the pretreatment step and decreases in lignin content %.
Figure 4:
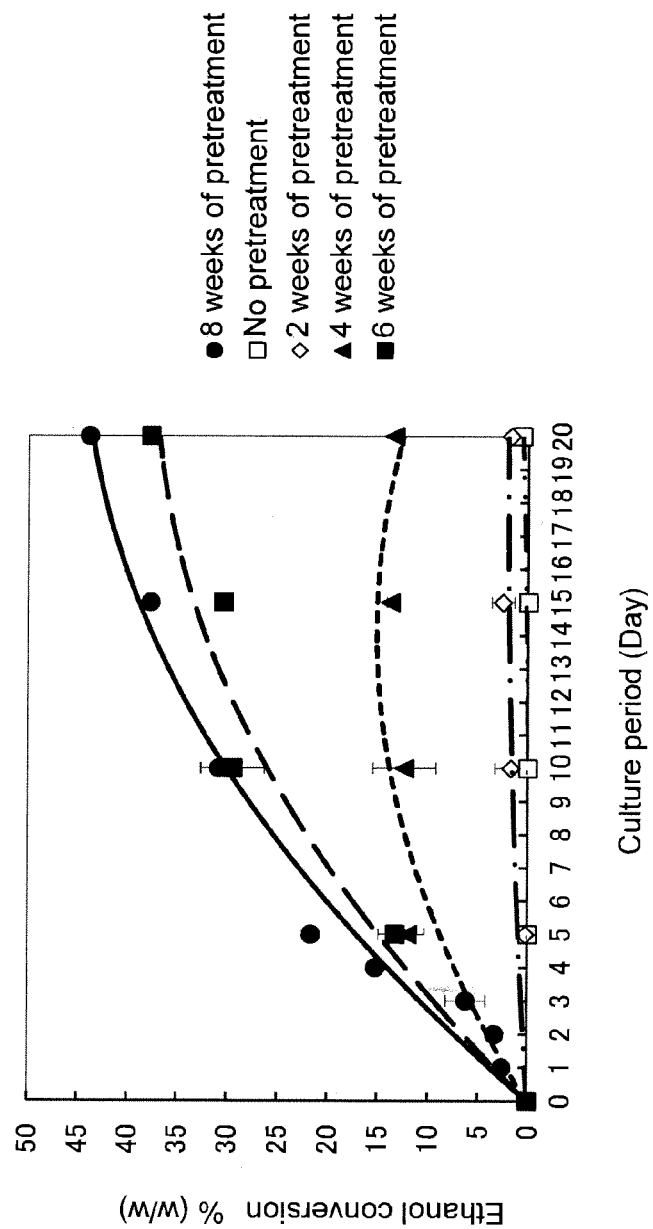
FIG. 4 is a graph showing the relationship between the period of the fermentation step and ethanol conversion %.

The results of the pretreatment step are shown in Table 3 and FIG. 3, and the results of the fermentation step are shown in Table 4 and FIG. 4.

Whereas the lignin content in untreated wood flour was 23.1%, the lignin contents were found to decrease to 18.1% and 13.7%, when culture was performed under aerobic conditions for 4 weeks and 8 weeks, respectively. Meanwhile, when the polysaccharide content in wood flour was calculated on the basis of the monosaccharide content in a product hydrolyzed with sulfuric acid. As a result, the glucan content was found to relatively increase. Specifically, it was demonstrated that delignification with high selectivity had been conducted.

Samples cultured for 2, 4, 6, and 8 weeks under aerobic conditions were each cultured under semi-aerobic conditions (switched from aerobic conditions). The longer the culture period under aerobic conditions, the greater the amount of ethanol generated. The theoretical ethanol yield of 37.7% was obtained from wood flour treated by performing 6 weeks of culture (pretreatment) under aerobic conditions and then 20 days of culture under semi-aerobic conditions. A theoretical ethanol yield of 43.9% was obtained from wood flour treated by performing 8 weeks of pretreatment under aerobic conditions and 20 days of culture under semi-aerobic conditions.

These results indicate that the *Phlebia* sp. MKFC40001 alone can perform delignification, saccharification and fermentation within a single reactor.

TABLE 3

Changes in chemical composition of wood flour during pretreatment (aerobic delignification)

| Pretreatment period (Week) | Content (% w/w) | | | | | |
|---|---|---|---|---|---|---|
| | Glucan | Xylan | Galactan | Mannan | Lignin | Others |
| 0 | 38.69 | 13.19 | 1.01 | 1.75 | 23.11 | 22.3 |
| 2 | 37.34 | 12.18 | 0.98 | 1.70 | 21.67 | 26.1 |
| 4 | 41.55 | 13.27 | 0.90 | 1.83 | 18.11 | 24.3 |
| 6 | 42.91 | 12.35 | 0.78 | 1.75 | 15.18 | 27.0 |
| 8 | 39.42 | 10.73 | 0.71 | 1.65 | 13.70 | 33.8 |

Values in the table were obtained by HPLC analysis of reducing sugar obtained from samples after each pretreatment (sulfuric acid hydrolysis) and then expressed in terms of polymer.

TABLE 4

Relationship (ethanol yield %) between pretreatment period and fermentation ability

| Fermentation period (day) | Pretreatment period (Week) | | | | |
|---|---|---|---|---|---|
| | 0 | 2 | 4 | 6 | 8 |
| 0 | 0 | 0 | 0 | 0 | 0 |
| 5 | 0 | 0.2 | 12.0 | 13.2 | 21.6 |
| 10 | 0 | 1.7 | 12.3 | 29.4 | 30.8 |
| 15 | 0 | 2.5 | 13.8 | 30.4 | 37.7 |
| 20 | 0.6 | 1.7 | 13.4 | 37.7 | 43.9 |

The theoretical ethanol yield calculated from the sugar composition (Table 3) of a substrate after each pretreatment was determined to be 100% and then the actually generated ethanol yield was calculated based thereon.

All publications, patents, and patent applications cited in this description are herein incorporated by reference in their entirety.

The invention claimed is:

1. A method for producing ethanol comprising:
   a pretreatment step for culturing a basidiomycete belonging to the genus *Phlebia* with a carbon source under aerobic conditions; and
   a fermentation step for further culturing the basidiomycete with the carbon source under semi-aerobic conditions or anaerobic conditions after the pretreatment step, so as to generate ethanol,
   wherein the pretreatment step and the fermentation step are performed within the same reactor.

2. The method according to claim 1, wherein the basidiomycete belonging to the genus *Phlebia* is *Phlebia* sp. MKFC40001 (NITE BP-1099).

3. The method according to claim 1, wherein the carbon source is a polysaccharide.

4. The method according to claim 3, wherein the polysaccharide is in the form of a plant biomass material, crystalline cellulose, paper, pulp, or cotton linter.

5. The method according to claim 1, wherein the carbon source is at least one type of saccharides selected from the group consisting of glucose, xylose, mannose, galactose, fructose, and arabinose.

* * * * *